United States Patent [19]

Harada et al.

[11] Patent Number: 4,571,376
[45] Date of Patent: Feb. 18, 1986

[54] COLOR DIFFUSION TRANSFER PHOTOGRAPHIC FILM UNIT WITH 1-M-(METHYL OR ETHYL)PHENYL-4-METHYL-4-HYDROXYMETHYL PYRAZOLIDINONES

[75] Inventors: Tōru Harada; Shigeo Hirano; Shigeru Nakamura, all of Kanagawa; Isao Shimamura, Tokyo, all of Japan

[73] Assignee: Fuji Photo Film Co., Ltd., Kanagawa, Japan

[21] Appl. No.: 746,481

[22] Filed: Jun. 19, 1985

[30] Foreign Application Priority Data

Jun. 19, 1984 [JP] Japan .................. 59-126268

[51] Int. Cl.$^4$ ............... G03C 1/40; G03C 5/30; G03C 5/54
[52] U.S. Cl. .................. 430/218; 430/440; 430/480; 430/483
[58] Field of Search ............ 430/218, 440, 483, 480

[56] References Cited

U.S. PATENT DOCUMENTS

| | | | |
|---|---|---|---|
| 3,247,201 | 4/1966 | Demarle et al. | 430/483 |
| 3,453,109 | 7/1969 | Lee | 430/483 |
| 4,209,580 | 6/1980 | McCreary et al. | 430/218 |
| 4,463,081 | 7/1984 | Michno et al. | 430/218 |
| 4,471,045 | 9/1984 | Bodem et al. | 430/218 |

Primary Examiner—Richard L. Schilling
Attorney, Agent, or Firm—Sughrue, Mion, Zinn, Macpeak and Seas

[57] ABSTRACT

A color diffusion photographic film unit comprising (a) a light sensitive element comprising at least one photosensitive silver halide emulsion layer associated with a redox compound adapted to release a diffusible dye, (b) an image receiving element, and (c) an alkaline processing composition element, wherein a 1-m-alkyl-substituted phenyl-3-pyrazolidinone electron transfer agent of the following general formula (I) or a precursor thereof is incorporated in at least one of said elements (a) through (c)

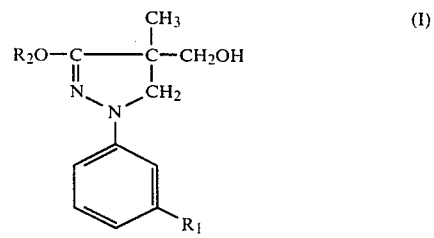

wherein $R_1$ is methyl or ethyl and $R_2$ is hydrogen or a group cleavable under alkaline conditions is disclosed.

14 Claims, No Drawings

COLOR DIFFUSION TRANSFER PHOTOGRAPHIC FILM UNIT WITH 1-M-(METHYL OR ETHYL)PHENYL-4-METHYL-4-HYDROXYMETHYL PYRAZOLIDINONES

FIELD OF THE INVENTION

This invention relates to the art of photography and more particularly to a film unit for color diffusion transfer photography.

BACKGROUND OF THE INVENTION

In color diffusion transfer photography, the so-called redox compound (hereinafter, "DRR compound") which releases a diffusible dye has been used as the color image reproduction material (hereinafter "dye material"). *Photographic Science and Engineering*, 20, No. 4 July/August, 1976, P. 155-160 and T. H. James et al.: *The Theory of The Photographic Process*, The MacMillan Publishing Co., Inc., Third Edition, P. 300 and Fourth Edition (1977), P. 322 state that in order to cause a DRR compound to release a diffusible dye in an imagewise pattern corresponding to the exposure of the silver halide, it is advantageous to employ a derivative of 1-phenyl-3-pyrazolidone (pyrazolidinone), particularly 1-p-methylphenyl-4-methyl-4-hydroxymethyl-3-pyrazolidone, as an electron transfer agent. The rationale of using such an electron transfer agent is that not only a high level of development activity can be assured but the compound itself is readily soluble and stable in alkaline processing compositions.

U.S. Pat. No. 4,209,580 (corresponding to Japanese Patent Application (OPI) No. 52055/80 and European Patent No. 0009837B1) also teaches that 1-p-methyl-m-methylphenyl-4-methyl-4-hydroxymethyl-3-pyrazolidone and 1-m,m'-dimethylphenyl-4-methyl-4-hydroxymethyl-3-pyrazolidone as well as precursors thereof can be used as electron transfer agents with the same advantageous as those referred to above.

However, irrespective of whether it is a "monosheet" type film unit comprising an image receiving element and a light sensitive element disposed in superimposition on a single support or a film unit such that an image receiving element and a light sensitive element are disposed on independent supports with a processing composition being spread between the two elements, the conventional film unit has the disadvantage that as the image receiving element carrying a diffusion transfer image is separated from the light sensitive element and the processing composition is exposed to the atmosphere, the 3-pyrazolidone (pyrazolidinone) type electron transfer agent contained therein gives rise to intense pink stains (as well as yellow stains depending on the compounds). This seriously detracts from the aesthetic quality of the transfer image.

SUMMARY OF THE INVENTION

It is an object of this invention to provide a film unit for color diffusion transfer photography which does not substantially give rise to pink and yellow stains when its image receiving element carrying a diffusion transfer image is separated from its light sensitive element and consequently the processing composition is exposed to air.

Other objects as well as numerous advantages of this invention will be readily understood by any one skilled in the art from the description of this invention that follows.

The above-mentioned objects have been met by this invention which provides a color diffusion transfer photographic film unit comprising (a) a light sensitive element comprising at least one light sensitive silver halide emulsion layer associated with a redox compound adapted to release a diffusible dye, (b) an image receiving element, (c) an alkaline processing composition element, wherein a 1-m-alkyl-substituted-phenyl-3-pyrazolidinone electron transfer agent of the following general formula (I) or a precursor thereof is incorporated in at least one of said elements (a) through (c).

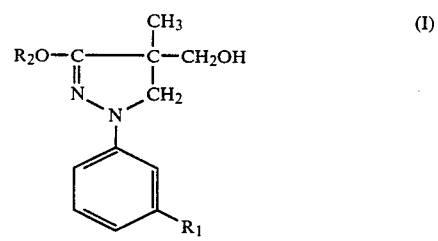

wherein $R_1$ is methyl or ethyl and $R_2$ is a hydrogen atom or a group cleavable under alkaline conditions.

DETAILED DESCRIPTION OF THE INVENTION

Referring to the above general formula (I) which stands for the electron transfer agent employable in the practice of this invention, the group cleavable under alkaline conditions $R_2$ is the so-called hydrolyzable group known in the art of photography and may for example be acetyl, mono-, di- or trichloroacetyl, perfluoroacyl, pyruvyl, alkoxyacyl, nitrobenzoyl, cyanobenzoyl, sulfonyl or sulfinyl. Preferably, $R_2$ is hydrogen, in which case the compound may exist either in the enol-form or in the keto-form.

The electron transfer agent of this invention can be synthesized, for example by the following route.

Reaction route

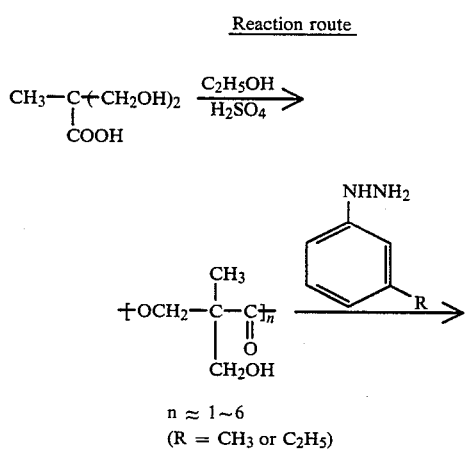

$n \approx 1{\sim}6$
$(R = CH_3 \text{ or } C_2H_5)$

-continued
Reaction route

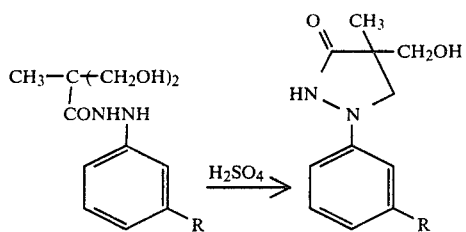

SYNTHESIS EXAMPLES

(1) Synthesis of 1-(2,2-dihydroxymethylpropionyl)-2-(m-methylphenyl)hydrazide A 2 l flask of egg plant shape is charged with 271 g of 2,2-dihydroxymethylpropionic acid, 540 ml of ethanol and 2.7 g of concentrated sulfuric acid and the mixture is heated at the boiling point of ethanol with stirring for 5 hours. Then, the reaction is conducted under reduced pressure (30–80 mmHg) for 3 hours. Thereafter, 270 ml of ethanol, 486 ml of SM-28 (Kawamura Riken, a 28% solution of sodium methoxide in methanol) and 247 g of m-methylphenylhydrazine are added and the reaction is continued for 4 hours, at the end of which time the reaction mixture is added to a mixture of 1.3 l of water and 240 ml of concentrated hydrochloric acid. The resulting crystals are recovered by filtration and recrystallized from n-hexane-ethyl acetate (1:1, v/v). Yield 265 g (55%).

(2) Synthetis of 4-hydroxymethyl-4-methyl-1-(m-methylphenyl)-3-pyrazolidone

A 2 l flask of egg plant shape is charged with 265 g of the product compound obtained in (1) above, 1.0 l of n-butanol and 12 g of concentrated sulfuric acid and the reaction is conducted at 120° C. for 3 hours. After completion of the reaction, the n-butanol is distilled off and the residue is crystallized by addition of 500 ml of n-hexane. The crystals are recovered by filtration and recrystallized from ethanol-n-hexane (3:5, v/v). Yield 168 g (74.3%); m.p. 110°–111° C.

The above electron transfer agent may be incorporated in any of the light-sensitive element, image-receiving element and alkaline processing composition element, although it is preferably incorporated in the alkaline processing composition element. Irrespective of which of said elements it is incorporated in, the electron transfer agent is preferably available in the light sensitive element in an amount of 0.2 to 2 g/m², more preferably 0.5 to 1 g/m².

Moreover, the use of this electron transfer agent in conjunction with some other 3-pyrazolidinone type developer (electron transfer agent) is more advantageous in that, for instance, the release of the diffusible dye from the dye material can then be promoted. Among the 3-pyrazolidinone developers that can be employed, 1-phenyl-4-methyl-4'-hydroxymethyl-3-pyrazolidinone is particularly desirable.

Such concomitant developer or electron transfer agent is advantageously used in a proportion of about 5 to 80 mole percent, preferably about 20 to 60 mole percent, relative to the electron transfer agent of this invention.

The processing composition which constitutes the alkaline processing composition element to be employed in the practice of this invention is a liquid composition containing an alkali donor substance and the solvent therefor is generally water and may include a hydrophilic solvent such as methanol, 2-methoxyethanol, etc.

The alkali donor substance is generally an alkali metal hydroxide and may for example be sodium hydroxide, potassium hydroxide, rubidium hydroxide or cesium hydroxide. Preferably, potassium hydroxide is employed.

The alkali donor substance is used in such an amount as to enable development of the silver halide and consequent release of a diffusible dye from the dye material and, further, enable diffusion and transfer of the dye so released. The concentration of the alkali is preferably not less than pH 13, more preferably pH 14.

It is also preferable to incorporate a thickener or viscosity builder in the alkaline processing composition. While suitable viscosity builders include ethers inert to alkaline solutions, such as hydroxyethylcellulose, and alkali metal salts of carboxymethylcellulose (e.g. sodium carboxymethylcellulose), hydroxyethylcellulose is particularly desirable. The viscosity builder is preferably added at the level of 1 to 10 weight percent of the whole processing composition. The viscosity to be established is preferably about 10,000 to 60,000 c.p.s.

Gradation control can be effected by using a competitive developer described in Research Disclosure No. 15162 (published November, 1976) in the alkaline processing composition. Hydroquinone, methylhydroquinone and t-butylhydroquinone, are examples of such competitive developer. A suitable amount of the competitive developer which can be used is from about 0.01 to 1 g/m², preferably from 0.1 to 0.5 g/m².

Furthermore, the compounds described in U.S. Pat. No. 2,497,917, for example 5-methyl-benzotriazole, 5,6-dichlorobenzotriazole, 6-nitro-benzimidazole and histidine, may also be incorporated.

It is also desirable to incorporate an opacifying agent such as carbon black, titanium dioxide, and a light absorbing dye (e.g. an indicator reagent). The indicator reagent is preferably a dye which remains transparent after exposure but produces a color or becomes opaque upon contact with alkali from the processing composition.

Furthermore, the incorporation of a sulfinic acid derivative is desirable in that, for instance, the inhibitory effect of the electron transfer agent of this invention on pink stains is potentiated. Examples of such sulfinic acid derivative include arylsulfinic acids (e.g. toluenesulfinic acid) and alkylsulfinic acids (the alkyl moiety of which contains 1 :o about 4 carbon atoms), which are soluble in the processing composition. The sulfinic acid derivative can be used in approximately the same proportional range as the electron transfer agent of this invention and while its ratio to the electron transfer agent of this invention may range from 0.1 to 10 times (by mole), they are preferably used in approximately equal amounts.

The support for at least one of the light sensitive element and image-receiving element used in the practice of this invention may be transparent or opaque but is preferably high in dimensional stability. Examples of such support include cellulose acetate film, polystyrene film, polyethylene terephthalate film, polycarbonate film, baryta paper, and paper laminated with a water-impermeable polymer such as polyethylene.

In order to obtain a white background, a whitening agent such as titanium oxide, barium sulfate or the like may be incorporated in the support or such a whitening agent may be coated over the support.

Furthermore, in order to enable development in a bright room, a light-screening effect may be imparted by using a laminate support including polyethylene containing an opacifying agent such as carbon black or a support coated with a dispersion of an opacifying agent such as carbon black in a water-soluble polymer vehicle (such as gelatin, polyvinyl alcohol, etc.). The level of addition of such opacifying agent can be selected according to the sensitivity of the light-sensitive material to be masked, and is preferably in the range of about 5 to 10 in optical density.

A neutralizing system is preferably provided in either the image receiving element (between the support and image receiving layer) or the light sensitive element (between the support and silver halide emulsion layer) of the film unit according to this invention. Such neutralizing system is generally comprised of a neutralizing layer and a neutralization timing layer associated therewith, although the neutralization timing layer is not essential.

It is preferable to use a film-forming acidic polymer for the neutralizing layer and the type of such an acidic polymer is virtually optional. Examples of acidic polymers which can be used in this invention include higher fatty acids, such as oleic acid, as disclosed in U.S. Pat. No. 2,983,606; polymers of acrylic acid, methacrylic acid or maleic acid or partial esters or anhydrides thereof, as disclosed in U.S. Pat. No. 3,362,819; copolymers of acrylic acid and acrylic acid esters, as disclosed in French Pat. No. 2,290,699; and latex-type acidic polymers, as disclosed in *Research Disclosure*, No. 16102 (1977) and U.S. Pat. No. 4,139,383. Specific examples thereof include copolymers of vinyl monomers (such as ethylene, vinyl acetate, vinylmethyl ester, etc.) and maleic anhydride and their n-butyl half esters; a copolymer of butyl acrylate and acrylic acid; and cellulose acetate hydrogen phthalate.

For the neutralization timing layer used in association with said neutralizing layer, there may be used such materials as, for example, gelatin, polyvinyl alcohol, polyacrylamide, partially hydrolyzed polyvinyl acetate, β-hydroxyethyl methacrylate-ethyl acrylate copolymer or cellulose acetate as a main component.

The image receiving layer constituting the image receiving element of this invention is preferably a hydrophilic colloid layer containing a dye mordant polymer layer.

Examples of such polymeric dye mordant used in accordance with this invention include secondary or tertiary amino group-containing polymers, polymers having a nitrogen-containing heterocycle moiety, quaternary cation group-containing polymers, etc., which have molecular weights in the range of 5,000 to 200,000 and, preferably, 10,000 to 50,000.

Among such mordants, those which do not readily migrate to other layers are preferred. Thus, mordants capable of cross-linking with the matrix such as gelatin, water-insoluble mordants, and latex dispersion (or aqueous sol) mordants are preferred.

The dye-providing (or-releasing) redox compound (DRR compound) that can be used in this invention may be either negative working or positive working, but negative working redox compounds are preferable.

The above-mentioned DRR compound may be represented by the following general formula:

Y-D wherein D represents a dye or dye precursor moiety and Y represents a group adapted to release a diffusible dye or dye precursor in an imagewise pattern as the result of development; Y and D may be linked through a suitable linking group.

Examples of Y are described in the literature such as U.S. Pat. Nos. 3,928,312, 3,993,638, 4,076,529, 4,152,153, 4,055,428, 4,053,312, 4,198,235, 4,179,291, 4,149,892, 3,844,785, 3,443,943, 3,751,406, 3,443,939, 3,443,940, 3,628,952, 3,980,479, 4,183,753, 4,142,891, 4,278,750, 4,139,379, 4,218,368, 3,421,964, 4,199,355, 4,199,354, 4,135,929, 4,336,322, 4,139,389, and Japanese Patent Application (OPI) Nos. 50736/78, 104343/76, 130122/79, 110827/78, 12642/81, 16131/81, 4043/82, 650/82, 20735/82, 69033/78, 130927/79, 164342/81 and 119345/82.

Among groups Y of negative working dye-releasing redox compounds, N-substituted sulfamoyl groups (N-substituents are groups derived from aromatic hydrocarbon rings or hetero-rings) may be mentioned. The following is a partial, and by no means exhaustive, list of groups Y.

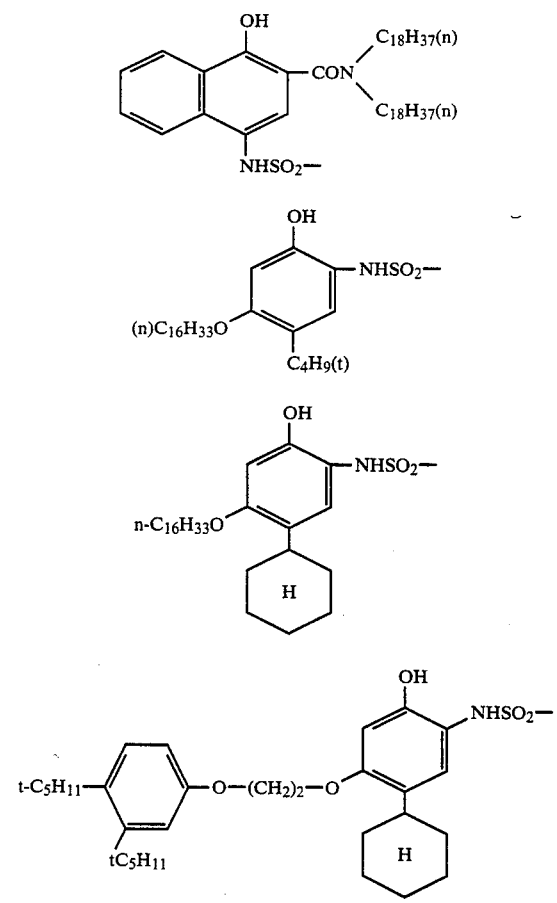

-continued

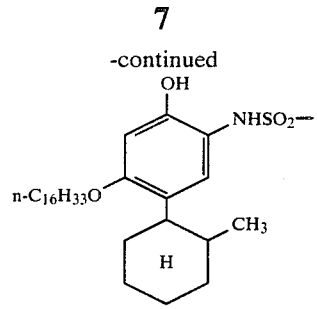

Examples of Y of positive working dye-releasing redox compounds are as follows.

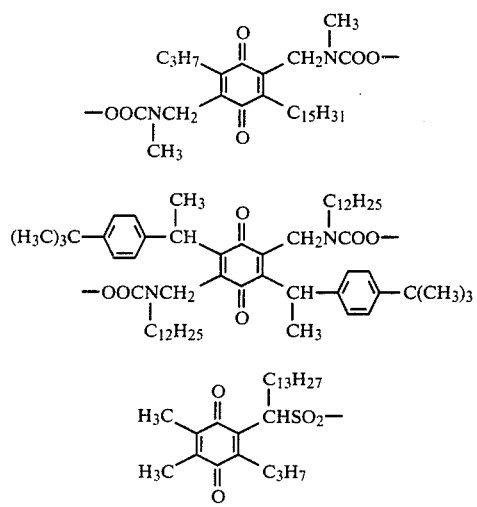

This type of compound, if used, is preferably used in conjunction with a diffusion-resistant electron donor compound (known as ED compound) or a precursor thereof. Examples of such ED compound are given in U.S. Pat. Nos. 4,263,393 and 4,278,750, Japanese Patent Application (OPI) No. 138736/81, etc.

Examples of the dye D in the general formula shown above are described in the following literature.

EXAMPLES OF YELLOW DYE

U.S. Pat. Nos. 3,597,200, 3,309,199, 4,013,633, 4,245,028, 4,156,609, 4,139,383, 4,195,992, 4,148,641, 4,148,643, and 4,336,322; Japanese Patent Application (OPI) Nos. 114930/76 and 71072/81; *Research Disclosure*, 17630 (1978) and 16475 (1977).

EXAMPLES OF MAGENTA DYE

U.S. Pat. Nos. 3,453,107, 3,544,545, 3,932,380, 3,931,144, 3,932,308, 3,954,476, 4,233,237, 4,255,509, 4,250,246, 4,142,891, 4,207,104, and 4,287,292; Japanese Patent Application (OPI) Nos. 106,727/77, 106,727/77, 23,628/78, 36,804/80, 73,057/81, 71,060/81 and 134/80.

EXAMPLES OF CYAN DYE

U.S. Pat. Nos. 3,482,972, 3,929,760, 4,013,635, 4,268,625, 4,171,220, 4,242,435, 4,142,891, 4,195,994, 4,147,544, and 4,148,642; British Pat. No. 1,551,138; Japanese Patent Application (OPI) Nos. 99431/79, 8827/77, 47823/78, 143323/78, 99431/79 and 71061/81; European Pat. (EPC) No. 53,037 and No. 53,040; and *Research Disclosure*, 17,630 (1978) and 16,475 (1977).

The coating coverage of such DRR compound is about $1 \times 10^{-4}$ to $1 \times 10^{-2}$ moles/m², and, preferably, $2 \times 10^{-4}$ to $2 \times 10^{-3}$ moles/m².

The silver halide emulsion to be used in this invention is a hydrophilic colloid dispersion of silver chloride, silver bromide, silver bromochloride, silver bromoiodide or silver bromochloroiodide or a mixture thereof, and while the halogen composition may be selected according to the purpose of use of the light sensitive material as well as processing conditions, it is preferable to employ silver bromide, silver bromoiodide or silver bromochloroiodide, with an iodide content not exceeding 10 mole % and a chloride content not exceeding 30 mole percent.

As regards the crystal morphology of the silver halide grains, not only cubic, octahedral, tetradecahedral, spherical and other orthogonal grains but also tabular grains having an aspect ratio in excess of 5, which are described in *Research Disclosure*, 22534, January, 1983 and Japanese Patent Application (OPI) No. 108528/83, can be employed.

While this invention can be carried into practice using whichever of a surface latent image emulsion and an internal latent image emulsion, the use of an emulsion of the latter type is preferred.

In the photographic element according to this invention, the silver halide emulsion is used in association with the DRR compound. According to the intended color reproduction, a silver halide emulsion having a given color sensitivity and a dye with a given spectral absorption characteristic are used in the proper combination.

For the reproduction of natural color by substractive color photography, there is employed a light sensitive element comprising at least two sets each of an emulsion having a selective spectral sensitivity to a certain wavelength range and a DRR compound having a selective spectral absorption in the same wavelength range. Particularly, the combination of a blue-sensitive silver halide emulsion with a yellow DRR compound, the combination of a green-sensitive emulsion with a magenta DRR compound, and the combination of a red-sensitive emulsion with a cyan DRR compound can be employed with advantage. These emulsion-DRR compound combinations may be superimposed face to face in the light sensitive element or may be respectively formed into particles (the DRR compound and silver halide grains are present in the same particles) and together be coated as a single layer.

The silver halide emulsion may be incorporated in an interlayer of the photographic element as taught in U.S. Pat. No. 4,323,635.

Representative formats of the film unit according to this invention include the so-called "separable" format wherein the light sensitive element and image receiving element need not be separated throughout the course of exposure, development and viewing of the transfer image but if desired can be separated after completion of the transfer image (for example, the format described in Japanese Patent Application (OPI) No. 67840/81) and the so-called "peel-apart" format wherein after exposure of the light sensitive element the element is laminated face-to-face with the image receiving element and, after development of the silver image, the image receiving element (or a portion thereof) is separated from the light sensitive element (for example, the format disclosed in U.S. Pat. No. 2,983,606). Of course, the film unit of this invention may be provided in any other formats than the above-mentioned formats.

In any of such formats, the preferred procedure for the film unit of this invention is that after exposure of the light sensitive element, the film unit (the light sensitive element has been laminated with the image receiving element) is passed between a juxtaposed pair of pressor members at withdrawal thereof from the camera to destroy the pouch disposed between the light sensitive element and the image receiving element or a cover sheet, whereby the processing composition is released and spread over the interface to develop the exposed silver halide, after which the light sensitive element, etc. are separated from the image receiving element.

The following examples are provided for illustrative purposes only and are in no way intended to limit the scope of the present invention.

EXAMPLE 1

The following image receiving sheet, light sensitive sheet and processing composition were prepared.

Image receiving sheet

Paper support: A 150 μ-thick paper sheet laminated with 30 μ-thick polyethylene on either side. The polyethylene on the image receiving layer side contains titanium oxide as added in a proportion of 10% by weight relative to polyethylene.

Back side:
(a) An opaque layer consisting of 4.0 g/m² of carbon black and 2.0 g/m² of gelatin.
(b) A white layer composed of 8.0 g/m² of titanium oxide and 1.0 g/m² of gelatin.
(c) A protective layer of 0.6 g/m² of gelatin. The layers (a), (b) and (c) are superimposed in that order.

Image-receiving sheet:
(1) A neutralizing layer containing 22 g/m² of an acrylic acid-butyl acrylate (mol ratio 8:2) copolymer with an average molecular weight of 50,000.
(2) A neutralization timing layer containing a cellulose acetate of 51.3% acetylation (0.513 g of acetic acid is liberated from 1 g of a sample when hydrolyzed) and a styrene-maleic anhydride (mol ratio 1:1) copolymer with an average molecular weight of about 10,000 in a weight ratio of 95:5 and a total amount of 4.5 g/m².
(3) A layer containing a 6:4 blend of a polymer latex prepared by emulsion-polymerizing styrene-butyl acrylate-acrylic acid-N-methylolacrylamide in a weight ratio of 49.7/42.3/4/4 and a polymer latex prepared by emulsion-polymerizing methyl methacrylate, acrylic acid and N-methylolacrylamide in a weight ratio of 93:3:4 and with a total solid content of 1.6 g/m².
(4) An image-receiving layer coated using 3.0 g/m² of the following polymer and 3.0 g/m² of gelatin as coating assistant as well as the following compound:

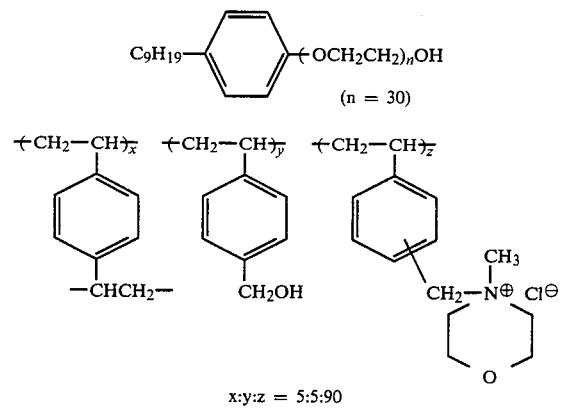

x:y:z = 5:5:90

Light-sensitive sheet

Each of the following layer dopes were coated on a transparent polyethylene terephthalate support to prepare a light-sensitive sheet.

Back side:
(a) An opaque layer containing 4.0 g/m² of carbon black and 2.0 g/m² of gelatin.

Emulsion layer side:
(1) A layer containing 0.44 g/m² of the following cyan dye releasing redox compound, 0.09 g/m² of tricyclohexyl phosphate, 0.008 g/m² of 2,5-di-t-pentadecylhydroquinone and 0.8 g/m² of gelatin.

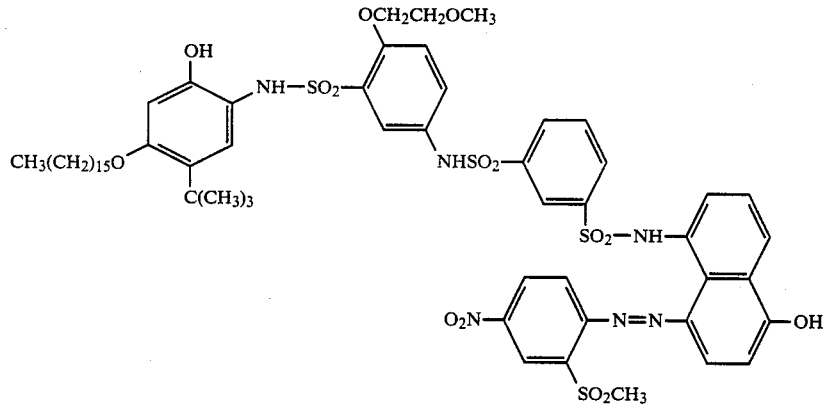

(2) A red-sensitive emulsion layer containing a red-sensitive internal latent image direct positive silver bromide emulsion (silver 1.03 g/m², gelatin 1.2 g/m²), 0.04 mg/m² of the following nucleating agent and 0.13 g/m² of 2-sulfo-5-n-pentadecylhydroquinone sodium.

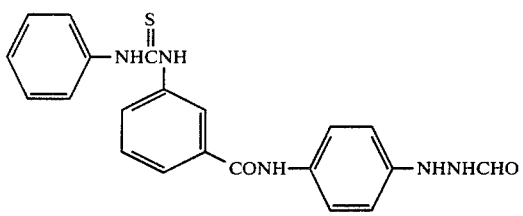

(3) A layer containing 0.43 g/m² of 2,5-di-t-pentadecylhydroquinone, 0.1 g/m² of trihexyl phosphate and 0.4 g/m² of gelatin.

(4) A layer containing 0.21 g/m² of a magenta dye releasing redox compound of the following structural formula I, 0.11 g/m² of a magenta dye releasing redox compound of the following structural formula II, 0.08 g/m² of tricyclohexyl phosphate, 0.009 g/m² of 2,5-di-t-pentadecylhydroquinone, and 0.9 g/m² of gelatin.

(8) A blue-sensitive emulsion layer containing a blue-sensitive internal latent image direct positive bromide emulsion (silver 1.09 g/m², gelatin 1.1 g/m²), 0.04 mg/m² of the same nucleating agent as used in layer (2) and 0.07 g/m² of 2-sulfo-5-n-pentadecylhydroquinone sodium.

(9) A layer containing 1.0 g/m² of gelatin.

| Processing composition | |
|---|---|
| ET (Table 1) | 36 mmol |
| Methylhydroquinone | 0.1 g |
| 5-Methylbenzotriazole | 5.0 g |
| Potassium sulfite (anhydrate) | 2.0 g |
| Hydroxyethylcellulose | 40 g |
| Potassium hydroxide | 56 g |
| Benzyl alcohol | 2.0 g |
| Water to make a total of 1 kg | |

After the above light-sensitive sheet was exposed through a color test chart, the image-receiving sheet was superimposed on it, and the above processing com-

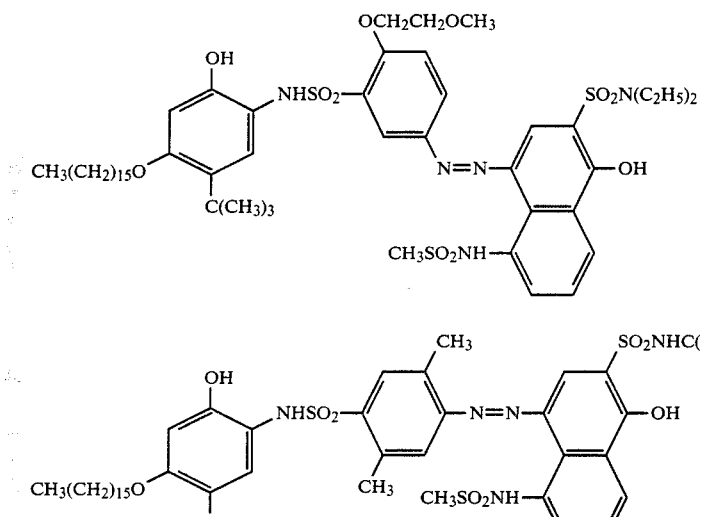

Structural formula I

Structural formula II (5) A green-sensitive emulsion layer containing a green-sensitive internal latent image direct positive silver bromide emulsion (silver 0.82 g/m² and gelatin 0.9 g/m²), 0.03 mg/m² of the same nucleating agent as used in layer (2), and 0.08 g/m² of 2-sulfo-5-n-pentadecylhydroquinone sodium.

(6) The same layer as layer (3).

(7) A layer containing 0.53 g/m² of a yellow dye releasing redox compound of the following structural formula, 0.13 g/m² of tricyclohexyl phosphate, 0.014 g/m² of 2,5-di-t-pentadecylhydroquinone and 0.7 g/m² of gelatin.

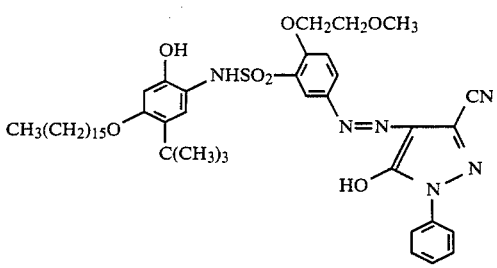

position was spread in a thickness of 65μ between the two sheets. (The spreading was done with the aid of a pressure roller).

The processing was carried out at 25° C. and after an interval of 90 seconds, the light-sensitive sheet was separated from the image-receiving sheet.

After separation, the time-course change in the maximum density of pink and yellow stains in the Dmin region was measured by means of a spectrophotometer equipped with an integrating sphere.

In addition, the time after development till separation was varied and the time in seconds (t 50%) required for the density in the maximum density area of the transfer image to reach one-half of the ultimate density was determined. The results are shown in the Table below.

TABLE 1

| ET | X | Pink stain Maximum density | Pink stain Half period (min) | Yellow stain Maximum density | Yellow stain Half period (min) | t 50% (seconds) |
|---|---|---|---|---|---|---|
| Compound of this invention | (A) m-CH$_3$ | 0.05 | 4 | 0.09 | 5 | 60 |
|  | (B) m-C$_2$H$_5$ | 0.06 | 4 | 0.08 | 5 | 62 |
| Control compound | (C) p-CH$_3$ | 0.17 | 7 | 0.09 | 5 | 55 |
|  | (D) 3,4-CH$_3$ | 0.14 | 4 | 0.09 | 3 | 57 |
|  | (E) 3,5-CH$_3$ | 0.05 | 5 | 0.23 | 20 | 65 |
|  | (F) H | 0.05 | 6 | 0.07 | 5 | 66 |

It will be apparent from the above table that compounds A and B of this invention are much less liable to cause pink and yellow stains that would develop transiently after separation of the sheets to detract from the quality of the transfer image. Moreover, as compared with control compound F showing the comparable degree of staining, the compounds of this invention are quick to complete the image as evidenced by their small t 50% values.

While the invention has been described in detail and with reference to specific embodiments thereof, it will be apparent to one skilled in the art that various changes and modifications can be made therein without departing from the spirit and scope thereof.

What is claimed is:

1. A color diffusion photographic film unit comprising (a) a light sensitive element comprising at least one photosensitive silver halide emulsion layer associated with a redox compound adapted to release a diffusible dye, (b) an image receiving element, and (c) an alkaline processing composition element, wherein a 1-m-alkyl-substituted phenyl-3-pyrazolidinone electron transfer agent of the following general formula (I) or a precursor thereof is incorporated in at least one of said elements (a) through (c)

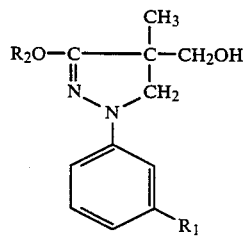
(I)

wherein R$_1$ is methyl or ethyl and R$_2$ is hydrogen or a group cleavable under alkaline conditions.

2. A color diffusion photographic film unit according to claim 1 wherein R$_2$ in the general formula (I) is hydrogen.

3. A color diffusion photographic film unit according to claim 1 wherein a sulfinic acid derivative is contained in the alkaline processing solution.

4. A color diffusion photographic film unit according to claim 1 wherein a neutralizing layer is provided in said image receiving element or said photosensitive element.

5. A color diffusion photographic film unit according to claim 1 wherein said image receiving element comprises a hydrophilic colloid layer containing a polymer mordant.

6. A color diffusion photographic film unit according to claim 1 wherein said redox compound adapted to release a diffusible dye is a negative working redox compound.

7. A color diffusion photographic film unit according to claim 1 wherein said 1-m-alkyl-substituted phenyl-3-pyrazolidinone electron transfer agent or said precursor thereof is used in combination with at least one other 3-pyrazolidinone electron transfer agent.

8. A color diffusion photographic film unit according to claim 7 wherein said other 3-pyrazolidinone electron transfer agent is used in a proportion of about 5 to 80 mole percent relative to said 1-m-alkyl substituted phenyl-3-pyrazolidinone electron transfer agent.

9. A color diffusion photographic film unit according to claim 7 wherein said other 3-pyrazolidinone developing agent is 1-phenyl-4-methyl-4'-hydroxymethyl-3-pyrazolidinone.

10. A color diffusion photographic film unit according to claim 8 wherein said other 3-pyrazolidinone electron transfer agent is used in a proportion of about 20–60 mole percent relative to said 1-m-alkyl-substituted phenyl-3-pyrazolidinone electron transfer agent.

11. A color diffusion photographic film unit according to claim 1 wherein R$_2$ is selected from the group consisting of acetyl, mono-, di- or trichloroacetyl, perfluoroacyl, pyruvyl, alkoxyacyl, nitrobenzoyl, cyanobenzoyl, sulfonyl and sulfinyl.

12. A color diffusion photographic film unit according to claim 1 wherein said electron transfer agent is incorporated in said alkaline processing composition element.

13. A color diffusion photographic film unit according to claim 1 wherein said electron transfer agent is available in the light sensitive element in an amount of 0.2 to 2 g/m$^2$.

14. A color diffusion photographic film unit according to claim 3 wherein the ratio of said sulfinic acid derivative to electron transfer agent is 0.1 to 10 by mole.

* * * * *